(12) United States Patent
Yang

(10) Patent No.: US 6,610,068 B1
(45) Date of Patent: Aug. 26, 2003

(54) NON-FLUSH OVER-THE-WIRE CATHETER DEVICES

(75) Inventor: Dachuan Yang, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 169 days.

(21) Appl. No.: 09/667,915

(22) Filed: Sep. 22, 2000

(51) Int. Cl.⁷ .................................................. A61F 11/00
(52) U.S. Cl. ........................................ 606/108; 604/96
(58) Field of Search ................. 606/108, 194, 606/151, 192

(56) References Cited

U.S. PATENT DOCUMENTS

| | | | |
|---|---|---|---|
| 5,047,045 A | 9/1991 | Arney et al. | 606/194 |
| 5,156,694 A | 10/1992 | Keith | 604/96 |
| 5,415,639 A | 5/1995 | VandenEinde et al. | 604/283 |
| 5,490,837 A | 2/1996 | Blaeser et al. | 604/96 |
| 5,534,007 A | 7/1996 | St. Germain et al. | 606/108 |
| 5,549,552 A | 8/1996 | Peters et al. | 604/96 |
| 5,598,844 A * | 2/1997 | Diaz et al. | 600/434 |
| 5,690,642 A | 11/1997 | Osborne et al. | 606/108 |
| 5,833,706 A | 11/1998 | St. Germain et al. | 606/194 |
| 5,980,533 A * | 11/1999 | Holman | 606/191 |
| 6,007,552 A | 12/1999 | Agro et al. | 604/264 |
| 6,024,918 A * | 2/2000 | Hendriks et al. | 422/44 |
| 6,066,118 A * | 5/2000 | Inoue et al. | 427/336 |
| 6,071,266 A | 6/2000 | Kelley | 604/265 |
| 6,086,547 A * | 7/2000 | Hanssen et al. | 600/585 |
| 6,090,126 A * | 7/2000 | Burns | 606/194 |
| 6,190,393 B1 * | 2/2001 | Bevier et al. | 604/96.01 |
| 6,280,413 B1 * | 8/2001 | Clark et al. | 604/102.01 |
| 6,306,144 B1 * | 10/2001 | Sydney et al. | 604/265 |

FOREIGN PATENT DOCUMENTS

WO      95/29722      11/1995

* cited by examiner

*Primary Examiner*—Michael J. Milano
*Assistant Examiner*—Victor Nguyen
(74) *Attorney, Agent, or Firm*—Vidas, Arrett & Steinkraus

(57) ABSTRACT

The present invention relates to a rapid exchange or single operator exchange catheter device comprising at least one elongated tubular member having an inner surface and an outer surface, a proximal and a distal end, and having an opening located between the proximal and the distal end. The inner surface of the elongated tubular member defines a guide member lumen and is at least occasionally subjected to contact with at least one guide member. The guide member lumen, including the opening or port for receiving the guide member, are filled with the lubricious material in accordance with the present invention. This method of filling the lumen eliminates the need for flushing the catheter device before and/or during surgical procedures to remove air and contaminants and provides a lubricant for easy maneuvering of the catheter over the guide member.

20 Claims, 5 Drawing Sheets

NON-FLUSH OVER-THE-WIRE CATHETER DEVICES

FIELD OF THE INVENTION

The present invention relates to medical devices used in combination with guide members. More specifically, the present invention relates to intravascular balloon dilatation catheters for use in combination with guide wires, and in particular, to those intravascular balloon dilatation catheters referred to as single-operator-exchange, rapid exchange or "monorail" catheters used in combination with guide wires. The inner surface of the catheter shaft which receives the guide member is filled with a lubricious material to eliminate the need for flushing the catheter device before surgical procedures. Those skilled in the art will recognize the benefits of applying the present invention to similar fields not discussed herein.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well-known in the art and typically involve the use of a balloon catheter with a guide wire, possibly in combination with other intravascular devices such as a stent. A catheter may also be used with a self-expanding stent alone. A typical catheter system has an elongate shaft with a device such as a balloon and/or stent attached to the distal end and a manifold attached to the proximal end. In use, the catheter is advanced over the guide wire such that the device positioned adjacent a restriction in a diseased vessel. The balloon is then inflated or the stent released and the restriction in the vessel is opened.

In particular, a typical angioplasty procedure requires inserting at least a guide catheter and a dilatation catheter into the vascular system of a patient to open a stenosis within that vascular system. There are two basic types of catheters used in combination with a guide wire. One type is an over-the-wire catheter. The second type is a modification of the basic over-the-wire catheter and is referred to as a single-operator-exchange (SOE) catheter or rapid exchange catheter. The construction and use of both OTW catheters and SOE catheters are well-known in the art.

The standard over-the-wire catheter has an inner or guide wire lumen that extends from the distal end of the catheter to the proximal end of the catheter. A manifold is attached at the proximal end of the catheter to provide an attachment for fluid communication with the guide wire lumen.

A single operator exchange catheter (SOE catheter), is a variation of the over-the-wire catheter. SOE catheters are commonly referred to in the art as rapid exchange catheters or "monorail" catheters. SOE catheters have a guide wire lumen that only extends through a portion of the catheter. The guide wire lumen extends from the distal end of the catheter to a distal porthole on the catheter tube.

An example of an OTW catheter may be found in U.S. Pat. No. 5,047,045 assigned to SCIMED Life Systems, Inc. Examples of SOE balloon catheters are disclosed U.S. Pat. No. 5,156,594 and U.S. Pat. No. 5,549,552 both also assigned to SCIMED Life Systems, Inc.

The guide wire lumen is provided for standard over-the-wire catheters and for SOE catheters so that a guide wire can be used to establish a path through the vascular system to the stenosis of the patient. The use of the guide wire enables the catheter to be advanced through the blood vessel relatively quickly, thereby reducing the time required for the procedure.

A concern that arises during an angioplasty procedure occurs when the operator attempts to load the guide wire into the catheter while the guide wire is in the vascular system of the patient. Generally, the relative diameters of the guide wire and the guide wire lumen make it difficult for the operator to load the guide wire into the inner or guide wire lumen. Once again, this problem is magnified by the fact that the angioplasty procedure is generally performed in a darkened room.

Typically therefore, before placing the catheter over the guidewire, it is desirable to flush the guidewire lumen with a flushing solution, generally a saline solution, to eliminate contaminants and air in the guidewire receiving lumen, as well as to lubricate the inner surface so that the catheter can be slid over the guidewire more easily.

The flushing procedure for a standard over-the-wire catheter is relatively simple because a luer-fitting is attached to the manifold on the proximal end of the guide wire lumen. The operator can simply attach a standard syringe to the proximal end of the guide wire lumen and force flushing fluid through the lumen. The flushing procedure for an SOE catheter is more difficult to perform because there is no fitting on either end of the guide wire lumen to connect a syringe to the guide wire lumen.

The procedure used for flushing a "rapid exchange" or "monorail" catheter typically involves the use of a blunt needle connected to a syringe. An operator, such as a nurse, inserts the blunt needle into the distal opening of the guidewire receiving lumen and then forces flushing fluid from the syringe, through the needle, into the distal opening of the guidewire receiving lumen and then forces flushing fluid from the syringe, through the needle, and into and through the inner or guidewire receiving lumen of the catheter.

The guide wire lumen of an angioplasty catheter is generally very small in size. For example, an angioplasty dilatation catheter having a guide wire lumen with a diameter as small as 0.016 inches is common in the medical industry. Therefore, it is very difficult to insert a lumen flushing needle (which commonly has an outside diameter of 0.012 inches) within the guide wire lumen of such a catheter. This problem is magnified by the fact that an angioplasty procedure is generally performed in a darkened room, making it very difficult to see the guide wire lumen of the catheter and the needle.

This procedure also creates a situation that is inherently dangerous to the operator. It is extremely easy for the operator to accidently stick a finger while attempting to insert the needle into the lumen ("needle stick"). Such an accident exposes the operator to a potential inadvertent transfer of dangerous or fatal diseases.

Using a needle and syringe can therefore be quite cumbersome, potentially dangerous and costly because the needle can puncture the balloon or the catheter, rendering the balloon catheter inoperable and increasing the risk to the patient.

Additionally, for some angioplasty procedures, more than one dilatating catheter having different balloon sizes or configurations may be used in a single procedure, or multiple stents may be inserted if the blockage is at a branch in a vessel, for instance. Therefore, it is common for the operator to remove a catheter from the vascular system and set that catheter aside to be reinserted at a later time in the procedure.

Another concern arises when the operator attempts to reinsert the catheter into the vascular system. This relates to the fact that the inner or guide wire lumen of the catheter has now been in fluid communication with the vascular system of the patient. Therefore, blood and other tissues from the patient may have collected within the guide wire lumen of the catheter. Such blood and tissue may coagulate and block the guide wire lumen of the catheter when the catheter is removed from the vascular system. The coagulated tissue then makes the catheter inoperable, since it prevents the operator from effectively guiding the catheter over the guide wire. Accordingly, the operator must flush the inner lumen of the catheter after removing it from the patient if the operator wants to reinsert the catheter later during the procedure.

There are numerous other medical procedures in addition to angioplasty that require an operator to use a lumen flushing technique similar to that described above. For example, some tissue collection procedures present the need for removing tissues from a collection chamber to perform further pathological studies on the tissue. There remains a need in the art for an efficient and effective means without exposing to the inherent dangers of the current needle-based method.

U.S. Pat. No. 5,598,844 describes a flushing device for use of "monorail" or "rapid exhcange" balloon catheters to solve the problems asociated with using a syringe and needle for flushing the guidewire receiving lumen of the catheter.

The present invention overcomes the aforementioned problems by filling the guide wire lumen with a lubricious material which eliminates the need for flushing prior to insertion of the catheter over the guide wire. This fills the excess space where air can get trapped and the lubricating qualities of the material also allows easy insertion of the guidewire through the shaft thereby removing the need for flushing with a saline solution or lubricant. The flushing step is thereby eliminated and consequently, the use of a needle and syringe is also eliminated.

SUMMARY OF THE INVENTION

The present invention relates to a non-flush catheter device comprising at least one elongated tubular member having an inner surface and an outer surface, a proximal and a distal end. The inner surface of the elongated tubular member defines a guide member lumen and is at least occasionally subjected to contact with at least one guide member. The guide member is filled with a lubricious material.

More specifically, the present invention relates to non-flush over the wire (OTW) catheter devices, and in particular to non-flush rapid exchange (RX) or single operator exchange (SOE) catheter devices. In an RX/SOE, the device comprises at least one elongated tubular member having an inner surface and an outer surface, a proximal end and a distal end, and an opening located between said proximal and distal end. The elongated tubular member has a guide member lumen therein. The inner surface of the elongated tubular member defines the guide member lumen and is at least occasionally subjected to contact with at least one guide member. The opening for receiving said guide member and the guide member lumen are filled with a lubricious material.

The lubricious material fills the excess space in the lumen thereby eliminating trapped air and lubricates the inner surface of the elongated tubular member thereby making insertion of the guide member easier. The lubricious material thereby eliminates the need for flushing the catheter device prior to insertion of the device over the guide member.

More specifically, the elongated tubular member is a catheter shaft. The catheter shaft may further comprise an inner shaft having an inlet port for receiving a guide wire.

In some specific embodiments, the tubular member comprises at least one thermoplastic polymer, and the guide member comprises at least one metal, or may be an alloy of metals.

Even more specifically, the present invention relates to an SOE or RX catheter device having proximal and distal ends comprising a polymeric shaft having an inner surface and proximal and distal ends. The shaft is open at the proximal and distal ends. A guide wire lumen is carried in the shaft and defined by the inner surface of the shaft. The shaft further has a guide wire port for receiving a guide wire, the port being located between the proximal and distal ends of the device. A lubricious material fills the guide wire lumen.

The present invention further relates to an SOE or RX non-flush catheter device comprising a sheath wherein a guide member is adapted to be inserted into a patient's vasculature so that a distal portion of the guide member is within the patient and a proximal portion thereof remains outside the patient. The sheath comprises an elongated tubular member having an inner surface defining a single longitudinally extending lumen sized to slidably receive a guide member therein. The tubular member has a distal insertion opening in communication with the lumen adjacent its distal end, a proximal insertion opening in communication with the lumen adjacent its proximal end, and a side hole port in communication with the lumen for receiving the guide member. The guide member lumen is filled with a lubricious material.

The lubricious material fills any excess space in the lumen of the devices described above, displacing the trapped air, preventing contaminants from reentering the device, and lubricating the inner surface of any elongated tubular member, shaft or sheath that defines the guide member lumen.

The present invention further relates to a method of eliminating the need for flushing a catheter device prior to insertion over a guide member and into the vasculature of a patient comprising the steps of providing a catheter shaft having an inner surface and an outer surface wherein the inner surface of the catheter shaft defines a guide wire lumen, filling the guide wire lumen with a lubricious material and storing the catheter device for a period of time prior to use. This latter step eliminates the need for flushing the device immediately prior to or during the surgical procedure.

DETAILED DESCRIPTIONS OF THE PREFERRED EMBODIMENTS

Figure 1:
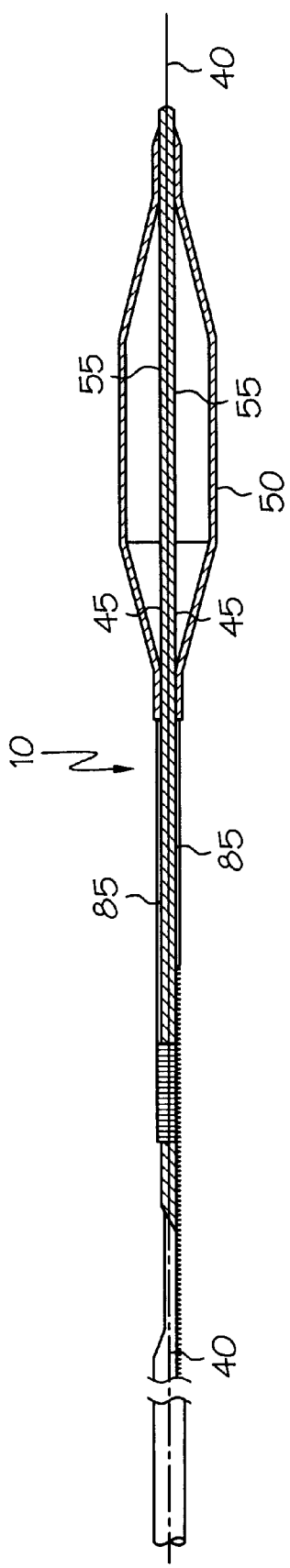
FIG. 1 is a sideview of a single operator exchange (SOE)/rapid exchange (RX) catheter device.

The present invention relates to over-the wire (OTW) catheter devices which in their broadest sense comprise an elongated tubular member through which a guide member, typically a metallic wire, is inserted. An inflatable balloon and/or stent may be mounted on the catheter device. Typically, a balloon will be connected to the distal ends of the inner tube and the outer tube. The guide member may be removed from and inserted into the guide member lumen at either end of the catheter. The elongated tubular member may also be described herein as a shaft or sheath.

In an OTW catheter device, the catheter in a broad sense, typically includes a lumen adapted to receive the guide wire from a proximal end to the distal end of the device. The guide wire is initially loaded through the lumen of the over-the-wire catheter and extends out from the distal end thereof.

More specifically, the present invention relates to single operator exchange (SOE) or rapid exchange (RX) catheter devices comprising an elongated tubular member. The elongated tubular member has an inner surface and an outer surface, the inner surface of the elongated tubular member defining the guide member lumen. The inner surface of the elongated tubular member is at least occasionally subjected to contact with at least one guide member. The tubular member has a proximal end and a distal end, and located between the proximal end and the distal end is a guide member port for receiving the guide member. In a typical SOE/RX construction, a guide wire occupies a position adjacent and exterior to the intravascular catheter along proximal and middle portions of the catheter and enters into a short guide wire lumen of the catheter via an opening at a location close to a distal portion of the catheter. With this type of construction, the catheter can be positioned in the patient's vessel by positioning a guide wire in the desired location and advancing the catheter device over the wire. Because the proximal end of the guide wire is exterior to the proximal end of the catheter, the proximal end of the guide wire can be held during withdrawal of the catheter so that the position of the distal end of the guide wire in the patient's vessel can be maintained. With this type of catheter, it is necessary that the distance from the distal end of the catheter to the proximal guide wire lumen entrance is less than the length of the guide wire that extends proximally out of the patient.

The guide member lumen is filled with a lubricious material according to the present invention which eliminates problems with trapped air and contaminants, as well as lubricating the inner surface of the tubular member which defines the guide wire lumen. This filling eliminates the need for flushing the catheter device prior to insertion over the guide member.

These devices may further include a balloon located at the distal end portion and/or a stent. If the device comprises a catheter balloon, the distal end portion will further have an inflation lumen for carrying fluid to the balloon for inflating the balloon. The device will also have an inner or guidewire receiving lumen for advancing the catheter over a guidewire. In an SOE/RX catheter system, the guide wire lumen is substantially shorter than the catheter itself.

The guidewire, previously inserted into a blood vessel in a person's body is placed into the inner or guidewire receiving lumen in the catheter. The guidewire receiving lumen in the catheter has a distal opening at a distal end of the catheter and a proximal opening located proximally of the distal opening at a cut away portion of the catheter.

The guidewire receiving lumen in the catheter extends along a distal end portion of the catheter only, unlike the outer lumen in the catheter which extends all the way from a proximal end of the catheter to the balloon at the distal end portion of the catheter.

The rapid exchange or monorail catheter is placed over a guidewire by placing a proximal end of the guidewire into the distal opening of the inner or guidewire receiving lumen and then pushing the catheter over the guidewire. The guidewire exits the guidewire receiving lumen of the catheter at the proximally located opening.

FIG. 1 represents generally at 10 a basic type of single operator exchange (SOE)/rapid exchange (RX) catheter device designed specifically as a dilatation catheter for an inflatable medical balloon designated 50. A guide wire lumen 45 is defined by a guide wire shaft 55. The lumen 45 is filled with a lubricious material 85 of the present invention. As can be seen from FIG. 1, a guide wire 40 extends through the guide wire lumen 45 defined by guide wire shaft 55 and filled with the lubricious material 85 according to the present invention.

Figure 2:
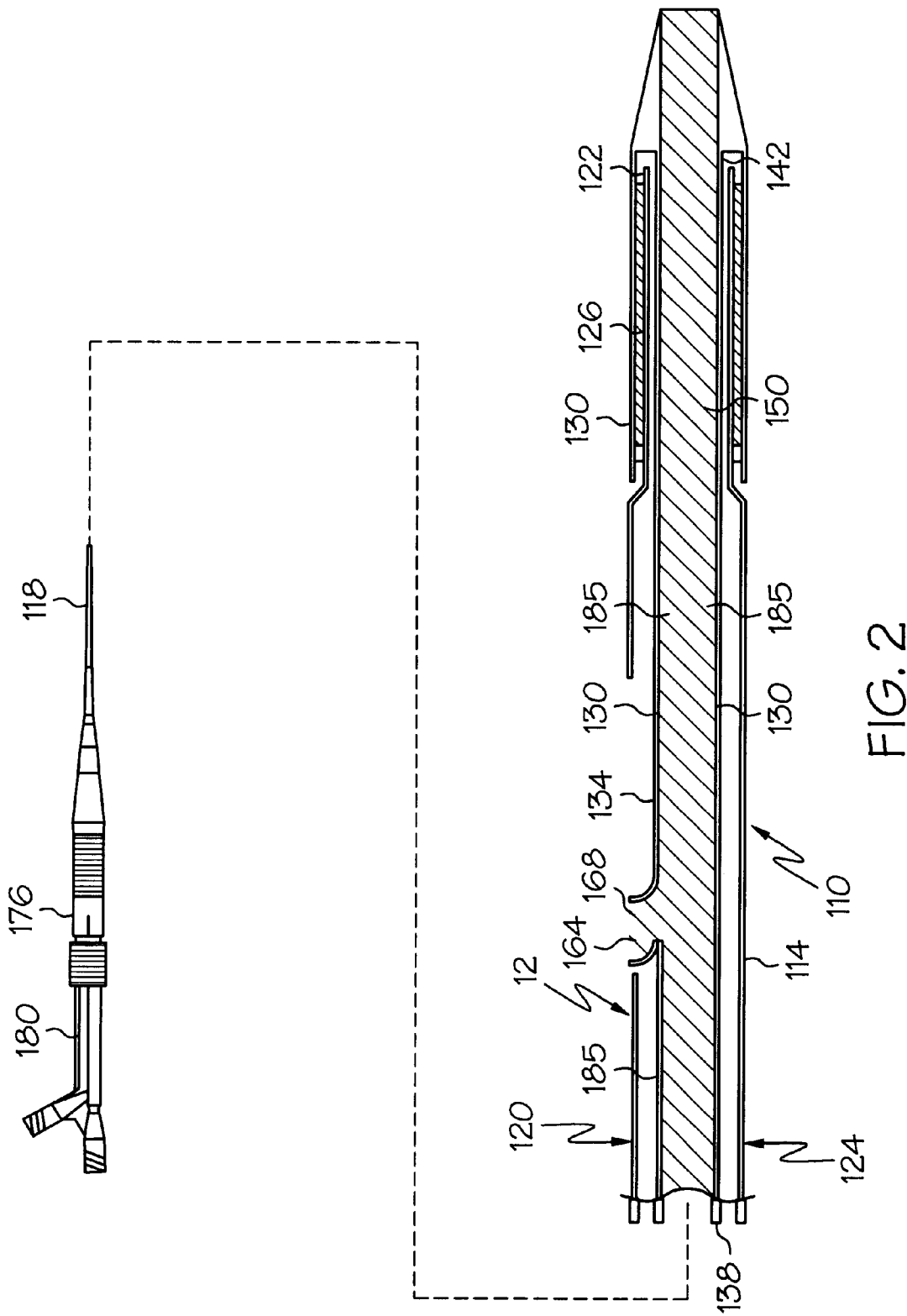
FIG. 2 shows a cross-sectional side view of a single operator exchange (SOE)/rapid exchange (RX) using the lubricious materials according to the present invention.

FIG. 2 illustrates generally at 110, a type of non-flush SOE/RX catheter device of the present invention. The device includes an elongated catheter shaft 114 having a proximal end 118 and a distal end 122, an inner surface 120 and an outer surface 124, and an opening 164 located between the proximal end and the distal end. At the distal end 122 of the elongated catheter shaft 114 is a mounting region 126 for mounting a treatment device 130, in this embodiment a stent, thereon. Elongated catheter shaft 114 has a lumen therein for receiving an inner shaft.

Inner shaft 134 (shown in FIG. 2) is movably carried within the elongated catheter shaft 114. Inner shaft 134 has a proximal end 138 and a distal end 142, and an inlet port 168 therein located between the proximal end 138 and the distal end 142 for receiving a guide wire (not shown) into the inner shaft 134. The opening 164 in the elongated catheter shaft 114 coincides with the inlet port 168 in the inner shaft 134 to allow the guide wire (not shown) to pass through the elongated catheter shaft 114 and into the inner shaft 134. The inner surface 138 of the inner shaft 134 defines the guide wire lumen 150. The guide wire lumen 150 is either partially or completely filled with the lubricious material 185 in accordance with the present invention. FIG. 2 shows the entire lumen 150 filled with the lubricious material 185.

In the SOE/RX embodiment, the guidewire runs within the catheter for only a short length. Coating 185 is shown throughout the guide wire lumen 150.

A manifold 176, including means to move the inner shaft through the elongated catheter shaft, is provided at the proximal end 118 of the medical treatment device delivery catheter.

An SOE/RX catheter of this type is described in detail in commonly assigned U.S. Pat. No. 5,980,533 herein incorporated by reference in its entirety.

Figure 3:
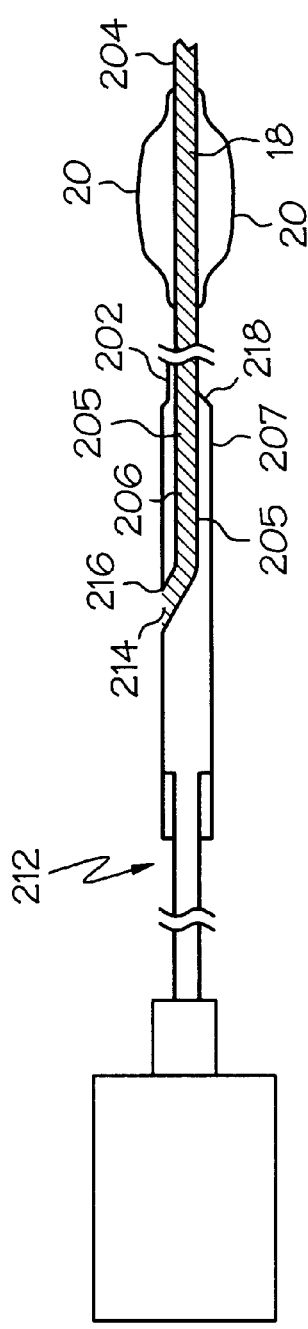
FIG. 3 shows a cross-sectional side elevational vies of another type of "rapid exchange" catheter using the lubricious materials according to the present invention.

FIG. 3 illustrates generally at 212 a different embodiment of an SOE/RX non-flush catheter delivery device. A single tubular member, i.e. the distal catheter shaft section 202, having an inner surface eliminates the need for a separate guide wire lumen and inflation lumen from a point proximal to the balloon through the balloon. The profile of a catheter designed in accordance with this embodiment is smaller and allows for better access to smaller vessels and better flow of fluid around the catheter 212, such as blood or radiopaque contrast fluid. During use, a guide wire (not shown) is disposed within the lumen 206 of the distal catheter shaft section 202 is provided. The guide wire lumen 206 defined by catheter shaft 207 of the distal catheter shaft section 202 is substantially filled with the lubricious material 205 in accordance with the present invention. SOE/RX catheters of a similar nature are discussed in U.S. Pat. No. 5,833,706 incorporated by reference in its entirety.

Figure 4:
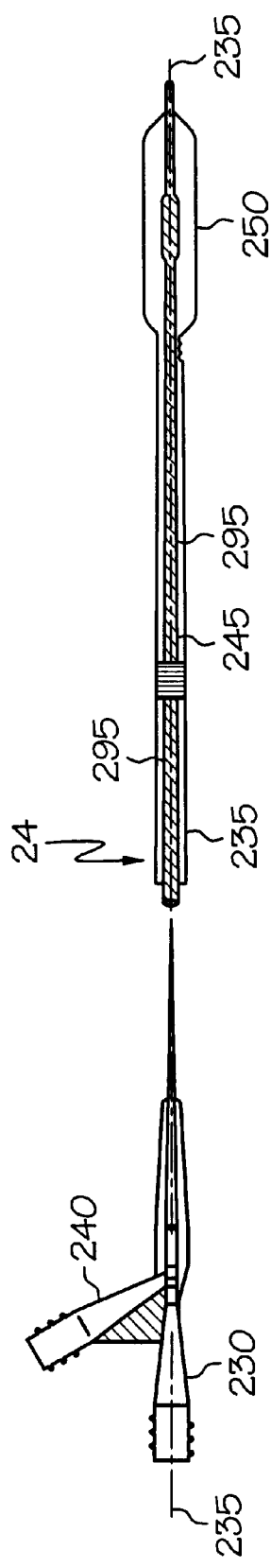
FIG. 4 shows a cross-sectonal side view of an over-the-wire dilatation catheter assembly designed specifically for an inflatable medical balloon using the lubricious materials according to the present invention.

FIG. 4 illustrates generally at 24 an over-the-wire catheter device designed specifically as a dilatation catheter for an inflatable medical balloon designated 250, for instance, an angioplasty balloon. The device comprises a manifold system designated generally at 230. The manifold 230 may further comprise a inflation luer 240. Guide wire 235 extends through the guide wire lumen 245 which is filled with the lubricious material 295 according to the present invention. The guide wire lumen 245 encloses the guide wire 235, which aids in the navigation of the catheter 24 through the appropriate vessel. The luer 240 may be partially filled or the inner surface coated with lubricious material.

Figure 5:
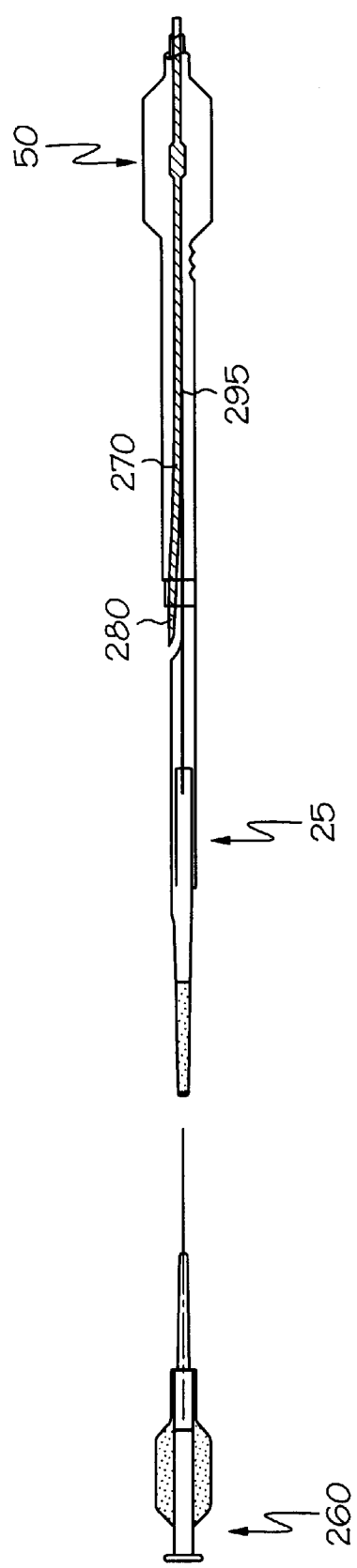
FIG. 5 shows a cross-sectional side view of an SOE/RX catheter device with a similar construction to the device shown in FIG. 5 using the lubricious materials according to the present invention.

FIG. 5 illustrates generally at 25 an SOE/RX catheter device similar in construction to the OTW device shown in FIG. 4, specifically designed as a dilatation catheter for an inflatable medical balloon 50. The device includes a guide wire lumen 270. The inner surface of the guide wire lumen 270, including the port 280 of the guide wire lumen, is filled with the lubricious material according to the present invention 295 to eliminate trapped air and to lubricate the inner surface without having to flush the device during a surgical procedure prior to insertion of a guide wire into the guide wire port 280 and advancement through the guide wire lumen 270.

Figure 6:
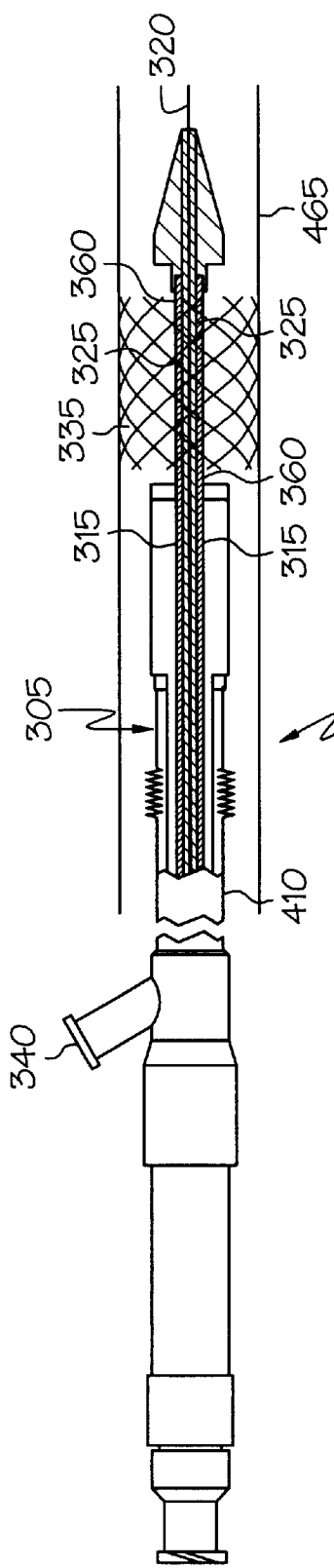
FIG. 6 shows a cross-sectional side view of an over-the-wire catheter assembly designed specifically for stent delivery using the lubricious materials according to the present invention.

FIG. 6 illustrates generally at 40 an over-the-wire catheter delivery device having a self-expanding stent 335 in a fully deployed position. A flexible outer sheath 410 comprises a guide wire lumen 315 defined by, in this construction, a flexible, but incompressible construction such as a polymer encapsulated braid or coil 360. However, other options are available and known to those of skill in the art.

The guide wire lumen 315 receives a guide wire 320 which aids in the navigation of the catheter 40 through the appropriate vessel. The guide wire lumen 315 is filled with the lubricious material 325 according to the present invention. This lubricious material eliminates the need for flushing the catheter prior to insertion over the guide wire 320. Additionally, the luer 340 may also be partially filled or the inner surface coated with lubricious material.

Figure 7:
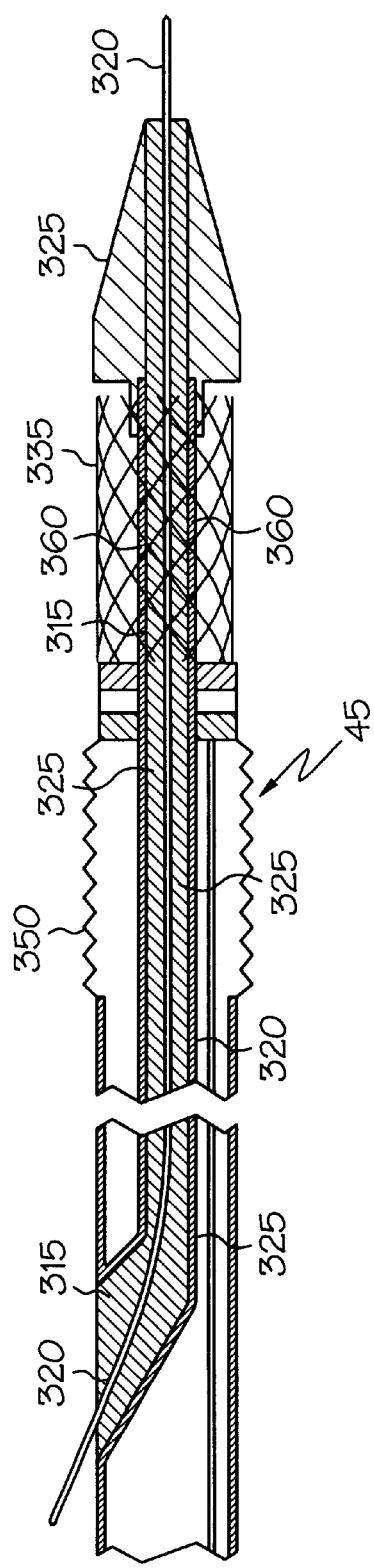
FIG. 7 shows a cross-sectional side view of an SOE/RX catheter having a construction similar to the device shown in FIG. 6 using the lubricious materials according to the present invention.

FIG. 7 illustrates generally at 45 an SOE/RX catheter device similar in construction to the OTW device shown in FIG. 6 and designed specifically for use with a self-expanding stent 335. The device comprises a guide wire lumen 315 defined by a guide wire shaft 360 which in this embodiment may be constructed of a flexible, but incompressible construction such as a polymer encapsulated braid or coil. The guide wire lumen 315 carries a guide wire 320 which aids in the navigation of the catheter 45 through the appropriate vessel. The guide wire lumen 315 is filled with the lubricious material 325 according to the present invention which aids in lubrication and navigation of the catheter 40 over the guide member 320 and through the vasculature of the patient, and eliminates the problem of trapped air thus eliminating the need for an operator to flush the catheter device 45 prior to insertion over the guide member 320.

OTW and SOE/RX devices of this construction type are discussed in detail in U.S. Pat. No. 5,534,007 incorporated herein by reference in its entirety.

For a more detailed discussion of SOE/RX catheters, see for instance, commonly assigned U.S. Pat. No. 5,415,639, U.S. Pat. No. 5,490,837, U.S. Pat. No. 5,534,007, U.S. Pat. No. 5,833,706, U.S. Pat. No. 5,980,533 and U.S. Pat. No. 6,007,522 all of which are incorporated herein by reference in their entirety. The construction and use of SOE/RX catheters is well known in the art.

Some embodiments of the OTW and SOE/RX catheter devices, along with lubricious materials useful herein, are described in detail in copending U.S. application Ser. No. 09/406,987 filed Sep. 28, 1999 incorporated herein by reference in its entirety.

The tubular member, also referred to herein as a shaft or sheath, of the present invention is typically manufactured of a thermoplastic polymeric material which is capable of being molded into a shaped polymeric tube. Such materials may include, but are not limited to, homopolymers, copolymers and terpolymers of ethylene; homopolymers, copolymers and terpolymers of propylene; polyesters; polyamides; polyimides; polyurethanes; vinylic copolymers; block copolymers; and so forth. For instance, materials as Nylon, Selar®, polyether-polyester block copolymers (i.e. Hytrel®), Pebax®, Surlyn®, polyethylene terephthalate, polytetrafluoroethylene, polyvinyl chloride, polyurethanes, polyetherurethanes, polyesterurethanes, polyurethane ureas, polyurethane siloxane block copolymers, polyethylene, polypropylene or other similar extrudable thermoplastic, polymeric materials, or composites thereof may be utilized in the present invention.

The lubricious materials useful herein include both hydrophobic and hydrophilic materials. The hydrophobic materials useful herein include, but are not limited to, silicone based lubricants, glycerine, olive oil, cottonseed oil, peanut oil, fish oil, vegetable oil, sesame oil, vitamin E, and so forth.

There are various types of hydrophilic polymers which may be useful to the present invention including both non-reactive and reactive. Hydrophilicity may also be obtained by the reaction of polymers in the presence of water which then subsequently form water soluble moieties. The hydrophilic lubricants useful herein include polyalkylene glycols, alkoxy polyalkylene glycols, polyalkylene oxide modified polydimethylsiloxanes, copolymers of methylvinyl ether and maleic acid, poly(vinylpyrrolidone), poly (acrylamide) including poly(N-alkylacrylamide), poly (acrylic acid), poly(saccharide), poly(vinyl alcohol), poly (ethyleneimine), polyamides, methyl cellulose, carboxymethylcellulose, polyvinylsulfonic acid, heparin, dextran, modified dextran, chondroitin sulphate, lecithin, copolymers thereof, and so forth. The polymers are typically chain-structured, non-crosslinked and water soluble having a hydrophilic group such as —OH, —CONH$_2$, —COOH, —NH$_2$, —COO—, —SO$_3$, —NR$_3^+$ and so forth where R is alkyl or hydrogen.

Derivatives of these polymers may also be utilized providing, even if they are not water soluble, that they are still of a structure which is capable of being hydrated, or is dispersible in water. Examples include esterified polymers, salts, amides, anhydrides, halides, ethers, hydrolyzates, acetals, formals, alkylols, quaternary polymers, diazos, hydrazides, sulfonates, nitrates, and ion complexes which are obtained by condensation, addition, substitution, oxidation, or reduction reactions of the above mentioned water soluble polymers. Also useful are polymers crosslinked with substances having more than one reactive functional group such as diazonium, azide isocyanate, acid chloride, acid anhydride, imino carbonate, amino, carboxyl, epoxy, hydroxyl and aldehyde groups. Further polymers include those copolymerized with vinyl, acrylic acid, methacrylic acid, diene compounds, and so forth.

A preferred class of hydrophilic lubricants are polyalkylene glycols or alkoxy polyalkylene glycols which have the following general formula:

$$R_1O(CH_2-CH_2-O)_x(CH(CH_3)-CH_2-O)_y(CH_2-CH_2-O)_zR_2$$

or $$RO-(CH(CH_3)-CH_2-O)_x(CH_2-CH_2-O)_y(CH(CH_3)-CH_2-O)_zR_2$$

R1 and R2 may be the same or different and can be H or an alkyl group having 1 to about 6 carbon atoms; x is from 2 to about 500; and y is from 0 to about 100.

The polyalkylene glycols and alkoxy polyalkylene glycols may also contain functional groups such as, for example, hydroxyl, sulfur, nitrogen or oxygen.

In a more specific preferred embodiment of the present invention, the water soluble lubricants are copolymers of polyalkylene glycols or alkoxy polyalkylene glycols. Specific examples of such copolymers include Pluronic® 31R1surfactant, a polyoxypropylene/polyoxyethylene block copolymer available from BASF Corp. in Mount Olive, N.J. and Cremophor® EL 35, an ethoxylated castor oil (PEG 35 Castor Oil) or polyoxyethyleneglycerol triricino available from BASF Corp. in Wyandotte, Mich.

Alternatively, the lubricious materials can be formed from hydrophobic compounds which can be converted to a lubricious hydrophilic compound through a chemical reaction such as hydrolysis, for instance. The conversion takes place after application of the lubricious material to the device. In this instance, the conversion will take place once the lumen has been filled with the lubricious material, either by injecting the material, or by coextruding it.

Examples of such compounds include those compounds having pendant ester or amide groups, such as, for instance, esters such as poly(acrylates), poly(meth)acrylates, poly (vinyl esters), poly(maleates), poly(fumerates), polyamides, poly(acrylamides), and copolymers and terpolymers thereof, and so forth. The poly(acrylic), poly(methacrylic) or polymaleic esters, and the polyamides or poly(acrylamides) may be converted to carboxylic acids by hydrolysis. Hydrolysis may be basic or acidic, and heat may be added to increase the rate of reaction. Esters are hydrolyzed reversibly in the presence of acid or irreversibly in the presence of base. The use of a large excess of water in the acid-catalyzed reaction favors hydrolysis. Vinyl esters may also be converted to an alcohol through saponification using an alkali-metal hydroxide which forms the alcohol and the metal salt of the acid. While most of these materials are hydrophobic, some are hydrophilic and can be hydrolyzed as well.

The following reaction schemes illustrate this embodiment of the present invention:

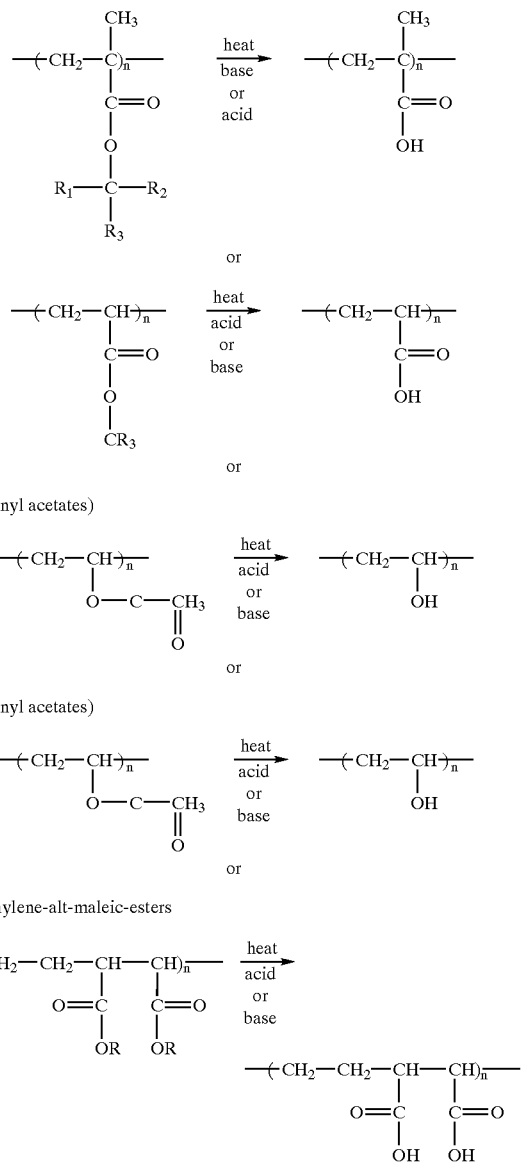

poly(vinyl acetates)

or poly(vinyl acetates)

or polyethylene-alt-maleic-esters

Where R, $R_1$, $R_2$ and $R_3$ can each independently be hydrogen or alkyl having from one to four carbon atoms and n is an integer. The molecular weight range for these polymers is broad and may be from about 800 to about 400,000 g/mole. Preferably, the molecular weights are from about 1,000 to about 20,000 g/mole.

While hydrophobic lubricants may be used, it is preferable to the present invention that a water sensitive or soluble lubricant be utilized. Water soluble lubricant quickly dissolve into the blood stream and move out of the body within a short period, reducing the likelihood of inflammation and restenosis.

It may be preferable to treat the surface to be coated (typically a polymeric surface) with a crosslinkable primer composition, in particular in those cases where a hydrophilic lubricant is used. It is desirable to maintain a lubricious layer on the inner surface of the shaft defining the guide member lumen even after the catheter has been inserted over the guide member. Hydrophilic materials are relatively soluble in bodily fluids and can be easily washed away or flushed from the surface. The primer will facilitate maintenance of a lubricious layer on the inner surface of the shaft defining the guide wire lumen for some period of time. The primer acts to promote adhesion of the hydrophilic coating to the inner surface of the shaft that defines the lumen.

Compounds useful in pretreating a surface include those having both hydrophobic and hydrophilic functionality thereon including those compounds having groups such as amine, amide, carboxyl, hydroxyl, and so forth. These groups are available on the surface for "binding" the water soluble lubricious material in such a way that it will not wash away from the surface of the article. This reactive primer provides a uniform wettable surface which facilitates adherence of the lubricious material along the interior surface of the tube.

Crosslinkable primers that are generally hydrophobic in nature but that have some some substituents attached thereon that make them attractive to hydrophilic polymers may be desirably utilized. It is surmised that a hydrophilic polymer will adhere to such a primer through hydrogen bonding. Therefore, any groups which participate in hydrogen bonding with the hydrophilic polymer will improve retention on the surface of the medical device.

The crosslinkable compounds include those having hydrophilic functionality such as amine, amide, carboxyl, hydroxyl, thiol, phosphorous, and so forth. The reactive primer is oriented in such a way that these functional groups provide a mechanism by which the water soluble lubricious material may better adhere to the surface to be lubricated, thereby preventing the water soluble lubricious material from immediately, or in any event prematurely, washing away upon exposure to bodily fluids, for instance.

A preferred class of crosslinkable compounds for use in pretreating the surface of the medical device are crosslinkable silicones, such as silane or silicone oligomers. However, other crosslinkable chemical agents may be utilized as well, providing that they contain substituents to form hydrogen bonding with the hydrophilic polymer. It is possible, and preferable, to utilize only a small amount of silicone for this purpose, reducing the possibility of irritation to sensitive tissues. Furthermore, because the silicone compound utilized in the present invention crosslinks, it tends to adhere better to the polymeric surface thereby further reducing the likelihood that any irritation will occur due to the silicone based compound. This silicone primer provides a an excellent foundation for the lubricious material, thereby improving both uniformity of the lubricious material and the long term stability. This stability ensures that there will be lubrication even after a relatively long shelf life.

In a preferred embodiment of the present invention, a silane having amino groups is utilized to adhere the hydrophilic polymer on the surface, thereby improving the retention of the lubricious material on the device.

More specifically, an example of a crosslinkable silicone surfactant useful to the present invention is a liquid silicone, amino-functional polydimethylsiloxane sold under the tradename of Dow Corning® MDX4-4159.

Other crosslinkable chemical compounds useful herein include titanate and zirconate coupling agents, such as isopropyl triisostearoyl titanate and neopentyl diallyl oxytrineodecanoyl zirconate. Both are available in liquid form.

These crosslinkable agents are often supplied in a solution with heptane and its mixtures, being a preferred solvent. These agents may be put in solution alone, and then coated on the medical device prior to application of the hydrophilic material, or they may be put in solution with the hydrophilic coating by using a cosolvent mixture, therefore eliminating one step in the manufacturing process.

Specific examples of primer compounds include silanes or silicone oligomers which form a crosslinked coating on the tubular surface upon application and drying. The silicone compound may be dissolved in a solvent, preferably heptane or the like in a concentration of about 0.1% to about 10% of the crosslinkable compound, preferably from about 0.2% to about 5% concentration based on weight/volume. The crosslinking reaction is carried out with heat at temperatures of about 30° C. to about 80° C., preferably from about 40° C. to about 65° C. and even more preferably at temperatures of about 45° C. to about 55° C.

Another method by which the inner surface of the tubular member may be treated to improve the adhesion of the hydrophilic material to the inner surface of the tubular member is to plasma treat the surface prior to filling the guide member lumen with the hydrophilic material. This type of surface treatment is designed to lower the surface energy (or raises the surface tension) of the polymeric surface being treated so that compounds can more easily wet out the surface. Using this surface modification method, the components can be loaded onto a manifold which is placed in a chamber through which gas is allowed to flow. The gas can flow through the inner surface of the component to be treated and over the outer surface of the component. In this manner, it is easy to treat the inner surface of these very small devices.

The gases useful in a plasma surface modification process include oxygen, fluorine, chlorine and gases having fluorine or chlorine atoms such as carbon tetrafluoride or carbon tetrachloride. These gases are used alone or in mixtures that may also contain argon, nitrogen, or carbon dioxide. Gases desirable for use in improving adhesion to plastic include oxygen, argon, nitrous oxide, helium and air. Chlorine and fluorine are considered highly toxic and hence are not as desirable for use.

Ammonia gases can also be used in plasma treatment methods to improve adhesion to plastic surfaces. Ammonia can be used alone or in combination with such gases as oxygen, nitrogen or argon.

One particular plasma treatment method useful herein uses a combination of oxygen and ammonia gases into a chamber within a predetermined pressure range creating a plasma discharge in the chamber.

Another specific embodiment involves the use of pure oxygen introduced at low pressure. Pure oxygen plasma has been known to improving the wettability of PTFE, for instance, although it is useful for other polymeric surfaces as well. High electrical potential across the electrodes in the chamber ionizes the gas mixture to form a chemically active plasma that removes material from exposed polymeric surfaces.

The water soluble or water sensitive lubricants are beneficial for use because they have the capability of quickly dissolving into the blood stream and moving out of the body within a short period, reducing the likelihood of inflammation and restenosis. Water soluble lubricants can exhibit excellent lubricity and friction reduction. Oil based lubricants such as silicones, glycerine or olive oil can bead and migrate from a surface, particularly in an aqueous environment, thus reducing the benefits of the lubricant on the surface.

Various solvents and their mixtures may be useful as the carrier of the lubricant. Preferably, the solvents are polar and include alcohols, glycols, water and so forth. Specific examples include ethanol, methanol, isopropyl alcohol (IPA), stearyl alcohol, ethylene glycol, propylene glycol, glycerin, water, methylethyl ketone (MEK) and so forth.

However, isopropanol and mixtures of isopropanol with other solvents, is preferred.

The lubricious material may also comprise Vitamin E which acts as an antioxidant. This improves the long term stability of the lubricious composition by reducing the degradation, allowing longer shelf stability. It is important that the lubricity of the medical device remains for an extended period to allow for the fact that such devices may not be used for a period of time. Vitamin E is sold in as a liquid and in itself has limited lubricious qualities and does not improve the overall lubricity of the composition. Vitamin E may be purchased from Sigma. Preferably, it will have a 95% purity or greater.

All of these various lubricious materials as well as the primer compositions are discussed in copending U.S. application Ser. No. 09/406,987 filed Sep. 28, 1999 incorporated herein by reference in its entirety.

The lumens may be filled with the lubricious materials according to the present invention using either an injection method, or by coextrusion, both of which can be done during the production of the catheter device.

The lubricious material may be prepared by making a solution of the lubricant in solvent at a concentration of about 1% to about 90% of the lubricant. Antioxidant may be added in an amount of about 0.01% to about 1.0% and preferably about 0.1% to about 0.5%. A preferable solvent for use with a lubricious hydrophilic material is an alcohol such as isopropanol, methanol or ethanol.

Alternatively, the lubricious material may be coextruded with the material from which the tubular member is being formed, such as polyethylene, Pebax®, polyester elastomer, and so forth, thereby forming a composite of layers or a tubular composite structure.

Using the method of the present invention eliminates the need for a saline solution or water flush of the device by the device operator immediately prior to, or during the medical procedure that is being undertaken. Further, it allows for storage of the device without the risk of trapped air or contaminants reentering the lumen.

The method of the present invention not only reduces the time required for the procedure, but also eliminates the risks inherent in using a needle during a flushing procedure. The catheter can therefore be inserted over the guide wire without a flushing step.

While some specific embodiments have been discussed herein, the invention is envisioned for use with any over the wire or rapid exchange catheter system. The method of the present invention is seen to be of benefit in any instance where it is necessary to utilize a guide member and possibly numerous catheters and/or catheter balloons wherein an operator is exchanging such devices during a single procedure.

Modifications of the invention not discussed herein are seen to be within the knowledge of one of ordinary skill in the art, and are consequently seen to be within the scope of the present invention.

What is claimed is:

1. A non-flush catheter device having a storage state and a use state, said device comprising at least one elongated tubular member having an inner surface and an outer surface, a proximal and a distal end, and wherein said inner surface of said elongated tubular member defines a guide member lumen and is at least occasionally subjected to contact with at least one guide member, said guide member lumen filled with a lubricious material throughout the storage state and the use state.

2. The catheter device of claim 1 wherein said device is a single operator exchange catheter device.

3. The catheter device of claim 2 wherein said elongated tubular member further has an opening located between said proximal end and distal end for receiving a guide member.

4. The device of claim 1 wherein said elongated tubular member is a catheter shaft and further comprises an inner shaft having an inlet port, said inlet port for receiving a guide member therein.

5. The device of claim 1 wherein said elongated tubular member comprises a thermoplastic polymeric material.

6. The device of claim 1 wherein said guide member comprises at least one metal or metal alloy.

7. The device of claim 1 wherein said lubricious material is selected from hydrophilic materials, hydrophobic materials, and mixtures thereof.

8. The device of claim 7 wherein said lubricious material is selected from polyalkylene glycols; alkoxy polyalkylene glycols; poly(saccharide); poly(vinylpyrrolidone); poly (vinyl alcohol); poly(acrylic acid); poly(acrylamide); poly (maleic anhydride); copolymers thereof and mixtures thereof.

9. The catheter device of claim 1 wherein said inner surface of said elongated tubular member defining said guide member lumen is pretreated with a reactive primer composition.

10. The catheter assembly of claim 9 wherein said reactive primer composition comprises at least one crosslinkable silicone compound.

11. The catheter device of claim 10 wherein said silicone compound comprises amino groups.

12. The catheter device of 10 wherein said silicone is a liquid amino polydimethylsiloxane.

13. The catheter device of claim 9 wherein said lubricious material comprises at least one hydrophilic compound which is an ethoxylated castor oil or a polyoxypropylene/polyoxyethylene copolymer.

14. The catheter device of claim 1 wherein said inner surface of said elongated tubular member defining said guide member lumen is pretreated with plasma.

15. The device of claim 1 wherein said device is a stent deployment device.

16. The device of claim 1 wherein said device is a dilatation catheter comprising an inflatable medical balloon.

17. The non-flush catheter device of claim 1 wherein during the use state, a guide wire is inserted through said guide wire lumen displacing some of said lubricious material.

18. A single operator exchange or rapid exchange non-flush catheter device having a storage state and a use state, said device having a proximal end and a distal end comprising a shaft having an inner surface and an outer surface, and proximal and distal ends, the shaft open at said proximal and distal ends, and carried in said shaft is a guide wire lumen defined by said inner surface of said shaft, said shaft having a guide wire port for receiving a guide wire located between said proximal and distal ends of said device, and filling said guide wire lumen is a lubricious material, said lumen filled with said lubricious material throughout the storage state and the use state.

19. A single operator exchange or rapid exchange non-flush catheter device having a storage state and a use state, said device comprising a sheath wherein a guide member is adapted to be inserted into a patient's vasculature so that a distal portion of the guide member is within the patient and a proximal portion thereof remains outside the patient, the sheath comprising an elongated tubular member having an inner surface defining a single longitudinally extending lumen sized to slidably receive a guide member therein, the tubular member having a distal insertion opening in communication with the lumen adjacent its distal end, a proximal insertion opening in communication with the lumen adjacent its proximal end, and having, a side hole port in communication with the lumen for receiving said guide member, and filling said lumen is a lubricant material, said lumen filled with said lubricant material throughout the storage state and the use state.

20. A non-flush catheter delivery device comprising at least one elongated tubular member having an inner surface and an outer surface, a proximal and a distal end, said inner surface of said elongated tubular member defines a guide member lumen and is at least occasionally subjected to contact with at least one guide member, and wherein said non-flush catheter delivery device is stored with said guide member lumen filled with a non-flowing lubricious material.

* * * * *